US008349189B2

(12) United States Patent  (10) Patent No.: US 8,349,189 B2
Anitua Aldecoa  (45) Date of Patent: Jan. 8, 2013

(54) METHOD FOR THE PREPARATION OF AT LEAST ONE COMPOUND FROM BLOOD, AND EXTRACTION DEVICE FOR USE IN THE EXECUTION OF SAID METHOD

(75) Inventor: Eduardo Anitua Aldecoa, Vitoria (ES)

(73) Assignee: Biotechnology Institute, I Mas D, S.L., Vitoria (ES)

( * ) Notice: Subject to any disclaimer, the term of this patent is extended or adjusted under 35 U.S.C. 154(b) by 349 days.

(21) Appl. No.: 12/780,287

(22) Filed: May 14, 2010

(65) Prior Publication Data

US 2010/0288706 A1   Nov. 18, 2010

(30) Foreign Application Priority Data

May 14, 2009 (ES) .................................. 200901227
Mar. 10, 2010 (ES) .................................. 201000306

(51) Int. Cl.
*B01D 21/00* (2006.01)
*B01D 21/01* (2006.01)
*B01D 21/26* (2006.01)
(52) U.S. Cl. ........ 210/696; 210/723; 210/787; 210/800; 210/808; 204/577; 204/579
(58) Field of Classification Search ............... 210/696, 210/723, 787, 800, 808; 600/577, 579
See application file for complete search history.

(56) References Cited

U.S. PATENT DOCUMENTS 5,450,856 A * 9/1995 Norris ........................... 600/577
6,569,204 B1 * 5/2003 Aldecoa ....................... 623/23.51

* cited by examiner

*Primary Examiner* — David A Reifsnyder
(74) *Attorney, Agent, or Firm* — Browdy and Neimark, PLLC

(57) ABSTRACT

Method for the preparation of at least one compound with biological properties from blood, where said method is performed in sealed tubes at a pressure below atmospheric pressure, thereby reducing or preventing the bacterial contamination of the compound through handling. The method comprises the repetition, for as many times as is required, of the following steps: connecting a second container that is vacuum-sealed to an extraction device connected in turn to a first container that contains blood separated into fractions, waiting for a period of time until the required fraction(s) is/are transferred, and removing said second container, with it thus being possible to obtain several second containers with different compounds for different medical applications including biological therapies. The steps may be performed in a closed system, without removing the caps of the containers, or alternatively the first container may be opened prior to the introduction of the extraction device.

13 Claims, 2 Drawing Sheets

METHOD FOR THE PREPARATION OF AT LEAST ONE COMPOUND FROM BLOOD, AND EXTRACTION DEVICE FOR USE IN THE EXECUTION OF SAID METHOD

TECHNICAL FIELD

The invention relates to a method for the preparation of at least one compound from blood, for example a compound rich in cell signals. The invention also relates to a device for use in the execution of the method.

PRIOR ART

U.S. Pat. No. 6,569,204 discloses a method for preparing a composition rich in growth factors from blood, which, over the course of time, has been shown to provide very interesting and beneficial biological properties for a variety of medical applications. This method, which may be performed in clinics (without the need for complex facilities or surgery), essentially comprises the following steps: the centrifugation of a tube containing blood and anticoagulant for a period of time and at a specific speed and temperature, the blood thereby being separated into different fractions; the extraction of the intermediate fraction, located above the red blood cells (lower fraction), where said intermediate fraction is a platelet-rich plasma; the transfer of said plasma to a second tube to which may be added calcium chloride, which acts as a coagulant and plasma activator (an agent capable of beginning the process whereby growth factors are released by the platelets); waiting for a certain period of time to allow the plasma to activate and to coagulate until the required consistency for the application is achieved. This composition has been used with favourable results in various medical fields such as bone regeneration (generally in implantology and traumatology), treatment of joint pain, skin treatment, etc. Some of them are described in U.S. Pat. No. 6,569,204 itself and in patent application US2009035382.

The method disclosed in U.S. Pat. No. 6,569,204 and many other known methods for the preparation of blood compounds with desirable biological properties involve a certain risk of the patient receiving the final compound becoming infected as, in some phases, they are not immune from bacterial contamination. There may be several reasons for said bacterial contamination: septicaemia that sends germs into the vascular stream, inadequate disinfection of the skin at the instant when the vein is punctured, or due to the handling of blood and subsequent compounds while the method is being performed. One of the factors contributing to the risk of bacterial contamination in handling procedures is the fact that the method disclosed in U.S. Pat. No. 6,569,204 and other methods are performed in open tubes, i.e. tubes that are not closed or vacuum-sealed, with the result that the centrifuged plasma and the compounds obtained during the process come into contact with the surrounding air (what is known as an "open circuit").

This invention aims to provide an improved procedure for the preparation of a compound with useful biological properties obtained from blood, where, among other advances in relation to known procedures, the risk of bacterial contamination of the final compound resulting from the handling of the blood and other subsequent substances during the course of the procedure is reduced, and the end product is stored in a sealed, sterile container.

BRIEF DISCLOSURE OF THE INVENTION

It is an object of the invention to provide a method for the preparation of at least one compound with desirable biological properties from blood, where said method uses vacuum-sealed tubes (i.e., tubes having an inner pressure that is below atmospheric pressure). For most of the duration of the method, and preferably for the entire duration, the plasma or any other compound involved in the method is prevented from coming into contact with the surrounding air. The method according to the invention guarantees to a greater extent the non-contamination of the final compound or compounds and their optimum medical and biological conditions.

The method of the present invention comprises the following steps: the disposal of a certain amount of blood in a first container that is vacuum-sealed (at a pressure below atmospheric pressure) and optionally contains anticoagulant; the separation of the blood into a series of fractions, one of them a plasma fraction with a platelet concentration gradient; the introduction of an extraction device substantially up to the top level of the highest fraction contained in the first container; the connection of a second container that is vacuum-sealed (at a pressure below atmospheric pressure and below that of the first container) to the first container and waiting for a certain period of time until a required amount of plasma and/or other fractions is/are transferred from the first container to the second container, as a result of the difference in pressures; and the removal of the second container. The steps involving the connection of the second container, waiting for a period of time and the removal of the second container may be repeated for the purposes of obtaining more than one second container (making sure that the depth to which the extraction device is inserted is adequately adjusted), each one containing a composition having a platelet concentration and other biological characteristics that are specific to the medical application for which it is to be used.

In one embodiment, all the steps are performed in a closed system, without the containers being opened or any other action being performed that causes the contents of the containers to come into contact with the surrounding air. In this embodiment, an air-venting system (allowing the intake of small amounts of filtered air) may optionally be inserted in the first container prior to the connection of the second container to the first container.

In another embodiment, the first container may be opened following the separation of blood into fractions and before the introduction of the extraction device, thereby simplifying the connection of the second container and the transfer of plasma and/or other fractions, as there is no need to perforate a cap with a Septum. This method may be equally secure in terms of the possible bacterial contamination of the compound when the first container is opened, prior to the transfer to the second container if, for example, the method is performed in a laminar flow chamber, in a sterile environment such as a surgery room. Furthermore, in many cases the final compound is applied in an open environment (for example in oral surgery or in the treatment of skin ulcers), as a result of which it is not even necessary to perform the method in a sterile environment.

The inventive procedure provides a number of interesting aspects and advantages over conventional procedures.

Firstly, the inventive method involves no automatic or compulsory extraction of the whole plasma fraction or various whole fractions. Instead, the inventive method allows the extraction, in sterile conditions, of the required amount of plasma and/or other fraction from the first container, depending on the application. In other words it is possible to extract the necessary quantities of plasma depending on the desired characteristics of the end product. As has been stated, it is also possible to obtain several second containers with different compounds for different medical applications from a single sample of blood (a single first container). The method thus enables the dose of platelets to be personalised along with any other required biological characteristics of the extracted fraction or fractions. This means that it is possible to tailor the final compound(s) to the medical applications for which they are designed.

Secondly, the product left in the second container is stored in a sealed and sterile container and is thus ready to receive subsequent treatments: further handling (e.g. the addition of an activating agent, waiting for a period of time, subjecting it to a certain temperature, further centrifugation, etc), infiltrations of other substances or products, storage, freezing, etc.

The compound manufactured in accordance with the method of the present invention may be used for various applications such as bone regeneration and the treatment of degenerative joint diseases.

BRIEF DESCRIPTION OF THE DRAWINGS

Details of the invention can be seen in the accompanying non-limiting figures.

DETAILED DISCLOSURE OF THE INVENTION

Figure 1:
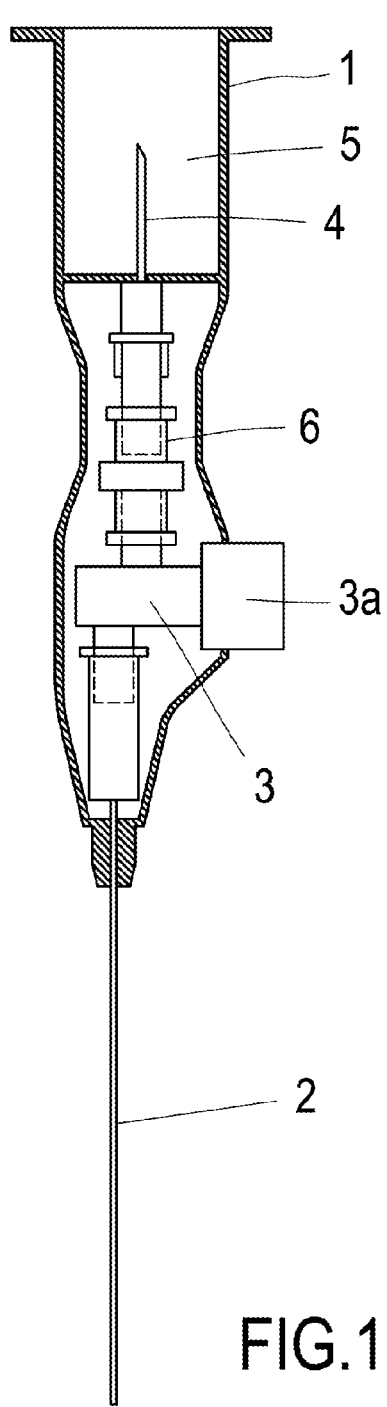
FIGS. 1 and 2 show a schematic view of an embodiment of the extraction device according to the invention, shown as an assembly and in breakdown form respectively.

The invention defines a method for the preparation of at least one compound from blood, the method comprising the following steps:

i) Providing a certain amount of blood in a first container that is vacuum-sealed, in other words, at a pressure below atmospheric pressure.

ii) Separating the blood into at least the following fractions: a fraction of red blood cells in the bottom part of the first container, a small fraction that contains white blood cells and platelets above the preceding one and, on top, a plasma fraction with a platelet concentration gradient, said gradient decreasing towards the top part of the first container (the plasma could even comprise, depending on the centrifugation conditions, a top part without platelets).

iii) Inserting an extraction device (catheter, needle or similar device) substantially up to the top level of the highest fraction contained in the first container.

iv) Performing, at least once, the steps of connecting a second container that is vacuum-sealed at a pressure below that of the first container to the extraction device; waiting for a certain period of time until a required amount of the plasma fraction, the fraction of white blood cells and platelets and/or the fraction of red blood cells is/are transferred, as a result of a difference in pressure, to the second container; removing the second container; and, in the event of further extractions being performed, adjusting the degree to which the extraction device is inserted so that it may once again reach the top level of the remaining fractions.

As a result, the invention allows obtaining a selective division of the various fractions of the first container (the plasma with the aforementioned concentration gradient, and/or other fractions).

With regard to the first step of the method, and in particular to the first container in which is a certain amount of blood is provided as the starting point for the method, said first container may present a series of specific characteristics.

In one embodiment, the first container is sealed and is not opened at any time, thereby creating a closed system or closed circuit in which the blood and other compounds obtained subsequently do not come into contact with the surrounding air without being filtered, thereby reducing the risk of bacterial contamination through handling, ensuring sterility and maintaining the biostability and biosecurity of the resulting end product. In this embodiment an air-venting system may optionally be introduced in the first container, thereby allowing the intake of filtered air in said container. In addition, the extraction device is preferably provided with a Septum to keep the circuit sealed.

In another embodiment, the first container is opened after the separation of the blood into fractions and before the introduction of the extraction device.

The first container is generally made of plastic or glass, and is sealed or capped with a screw-threaded or pressurised cap. The cap may be perforable to enable the sealed connection of the extraction device. In addition, the first container is preferably a cylindrical tube with a capacity of between 4 and 50 m.

Said first container may optionally contain at least one anticoagulant, depending on the subsequent use to be made of the compounds obtained as a result of the procedure. Sodium citrate is generally used as an anticoagulant as it is a natural component that can be found in the bloodstream and acts as a calcium divalent cation chelating agent (Ca 2+). However, other anticoagulants are also contemplated, such as EDTA, which is an artificial anticoagulant, although it is less specific for the calcium divalent cation (Ca 2+).

Examples of First Containers

The TE5 or TE9 PRGF® Collection Tubes, marketed by the applicant, are two examples of first containers that may be used with this invention. Both are sterile plastic tubes comprising a main body and perforable cap and have respective volumes of 5 and 9 ml. The use of either tube is determined by the requirements of the specific medical application, and both are labelled. Said labels comprise a scale indicating the volume and rising towards the bottom part of the tube. The tubes contain a 3.8% sodium citrate concentration as an anticoagulant and thus present the following characteristics:

| TE5 TUBE | |
|---|---|
| Capacity: | 5 ml |
| Vacuum volume (pressure): | 4.5 ml |
| Volume of sodium citrate: | 0.5 ml |
| Size: | 13 × 75 mm |
| TE9 TUBE | |
| Capacity: | 9 ml |
| Vacuum volume (pressure): | 8.1 ml |
| Volume of sodium citrate: | 0.9 ml |
| Size: | 16 × 100 mm |

Step two of the method involves the separation of the blood into different fractions, which is preferably carried out by centrifuging the first container (at a specific centrifugation speed and for a certain period of time) or by placing the tube in a rack and waiting for the fractions to separate by sedimentation.

In the event that the first container is centrifuged, said centrifugation may present a series of specific characteristics. The first container is preferably centrifuged at a speed of between 100 and 900 G for a time of 3 to 12 minutes and at an ambient temperature or not (i.e. at any temperature). Within these ranges, it is especially advantageous if centrifugation is carried out at a speed of between 300 and 800 G for a time of 5 to 9 minutes. These centrifugation parameter ranges separate the various fractions (plasma with varying platelet concentrates, white blood cells with platelets, red blood cells and others, if any) more clearly.

The step wherein an air-venting system is inserted in the first container is optional. If it is not inserted, plasma and/or another fraction is/are transferred until clinic staff remove the second container or until the pressure levels in the first and second container become the same (which depends on the pressure of the second container). If, however, an air-venting system is inserted, it allows filtered air to enter the sealed first container, as a result of which the pressure of the first container is always higher than the pressure of the second container. In consequence, extraction only ends when clinic staff removes the second container, when the extraction device is moved above the highest level, or when, of course, all the contents of the first container have been transferred to the second container.

With regard to the following steps involved in the method, relating to the insertion of an extraction device, the connection of a second container, the extraction of one part of the plasma or other fraction to the second container and the removal of said second container, said steps and the second container may present a series of specific characteristics.

The extraction device is inserted substantially up to the top level of the highest fraction contained in the first container. If a successive or sequenced extraction of different fractions to a series of second containers is performed, said extraction always involves the suction of the top part of the remaining liquid. In other words, the insertion of the extraction device is always adjusted to the top of the liquid as the level of liquid decreases during suction. Consequently, if for a specific medical application it is necessary, for example, to extract the bottom part of the plasma (the part with the highest concentration of platelets), first the plasma situated above the required part is extracted in one or various steps (this plasma, which contains a lower concentration of platelets, may be discarded or used for other medical applications).

The invention offers countless possibilities with regard to which fractions or combinations of fractions may be extracted. The following may be extracted: only plasma (all or part of the fraction, containing a variable concentration of platelets or even no platelets at all if centrifugation is carried out at high speed); only white blood cells with platelets (all or part of the fraction); only red blood cells (all or part of the fraction); plasma (all or part of the fraction) along with white blood cells (all or part of the fraction); plasma (all or part of the fraction) along with the whole fraction of white blood cells and part or all of the fraction of red blood cells; or part or all of the fraction of white blood cells along with part or all of the fraction of red blood cells.

In addition, the second container remains sealed and is not opened until at least the end of the procedure, thereby creating a closed system or closed circuit in which the plasma and other compounds do not come into contact with the air (as with the first container). Generally, it is sealed or capped with a screw-threaded or pressurised cap. The cap is perforable. The second container is preferably a cylindrical tube with a capacity of between 4 and 50 ml.

The second container may optionally contain at least one coagulant, procoagulant or platelet activator, depending on the requirements of the specific medical application for which the final compound is designed. A 10% calcium chloride concentration is generally used as a coagulant although other coagulants are contemplated, such as bovine thrombin, human thrombin, etc. The invention also contemplates the use, in the second container, of coagulation accelerators such as special inert additives that aid coagulation (silica, etc) and the fact that the second container is made of a coagulation accelerating material (glass). The invention also contemplates that the second container may contain other biomaterials or agents necessary for the medical application for which the compound contained in said second container is designed.

The coagulant, procoagulant, activating agent or other biomaterials or agents may be added to the second container before the transfer from the first container (e.g. during the manufacture of the second container), or once the transfer has been completed.

The second container is generally made of plastic or glass. Plastic may be useful for certain applications due to its ability to delay the coagulation process, an effect that is accentuated further if a second plastic container not containing a coagulant is used.

Examples of Second Containers

The TF5-EST or TF9-EST PRGF® Plasma Fractionation Tubes, marketed by the applicant, are two examples of second containers that may be used with this invention. Both are sterile plastic tubes comprising a main body and perforable cap and have respective volumes of 5 and 9 ml. The use of either tube is determined by the requirements of the specific medical application, and both are labelled. Said labels comprise a scale indicating the volume and rising towards the top part of the tube. These tubes have a different negative pressure and may be manufactured with different pressures according to technical requirements.

On another note, the invention contemplates that the extraction may be performed only once in order to separate a required amount from at least one fraction in a second container for a specific application. The invention also contemplates that this step may be repeated more than once in order to separate different parts of the plasma (with a different concentration of platelets or even without platelets) or other fractions in different second containers for different applications. For example, a part of plasma with a lower concentration of platelets or without platelets (the top part of the top fraction of the tube) may be extracted for an application and a part of plasma with a higher concentration of platelets (situated further down, closer to the fraction of white blood cells) may be extracted at a later stage for another specific application that requires an end product richer in cell signals, thereby making use of the platelet concentration gradient of the plasma fraction. Examples of procedures explaining the concept behind the inventive process of extraction are given below.

Example of Procedure 1

Blood is provided in a first container made of plastic without anticoagulant (the fact that anticoagulant is not used means that there is no need to use a coagulant and activator at a later stage). Following centrifugation, the whole plasma fraction is extracted to a second container made of glass, or to a second container made of plastic with a coagulation accelerator, with clot retraction being obtained thereby. The final compound has a semi-solid consistency and thus may be used as a fibrin cap or membrane in applications such as the stabilisation of a particulate bone graft prior to closing suturing in oral or maxillofacial surgery, for the treatment of a post-extraction alveolus, etc.

Example of Procedure 2

Blood is provided in a first container made of plastic without anticoagulant (the fact that anticoagulant is not used means that there is no need to use a coagulant and activator at a later stage). Following centrifugation, the whole plasma fraction is extracted to a second container made of plastic without coagulation accelerator, the coagulation of the plasma thereby being delayed. The final compound therefore has a liquid consistency and may be used for applications such as infiltration in articular tissue regeneration or in intradermal or intramuscular injections, or for its addition as a biomaterial in order to clot said biomaterial, etc.

Example of Procedure 3

Blood is provided in a first container made of plastic with anticoagulant (thereby delaying or preventing the coagulation). Following centrifugation:

Firstly, a certain amount of the top part of the plasma (in other words, a plasma with a lower concentration of platelets or without platelets) is extracted to a second container made of glass and comprising calcium chloride (coagulant and activator). A semi-solid compound is formed, which may be used as a fibrin cap in applications such as those referred to in example of procedure 1.

Secondly, the top part of the remaining plasma in the first container (in other words, a plasma with a higher concentration of platelets in relation to the plasma extracted beforehand) is extracted to another second container made of plastic and comprising calcium chloride (coagulant and activator). The calcium chloride may also be added at a later stage. A liquid compound is formed, which may be used for applications such as its mixture with autologous particulate bone from the patient (from whom the blood used in the method may be obtained) in an area of the body where bone is to be regenerated, for cutaneous and articular infiltration or any other use.

Example of Procedure 4

Blood is provided in a first container made of plastic and comprising anticoagulant. Following centrifugation, the whole plasma fraction is extracted to a second plastic container with a coagulant and activator. This agent may also be added at a later stage. The final compound has a liquid consistency and may be used for applications such as the infiltration of articular tissue, intradermal or intramuscular infiltrations, etc.

Example of Procedure 5

Blood is provided in a first container made of plastic without anticoagulant (the fact that anticoagulant is not used means that there is no need to use a coagulant and activator at a later stage). Following centrifugation, the first container is opened and the whole plasma fraction is extracted to a second container made of glass, or to a second container made of plastic comprising a coagulation accelerator, with clot retraction being obtained thereby. The final compound has a semi-solid consistency and thus may be used as a fibrin cap or membrane in applications such as the stabilisation of a particulate bone graft prior to closing suturing in oral or maxillofacial surgery, for the treatment of a post-extraction alveolus, etc.

Figure 2:
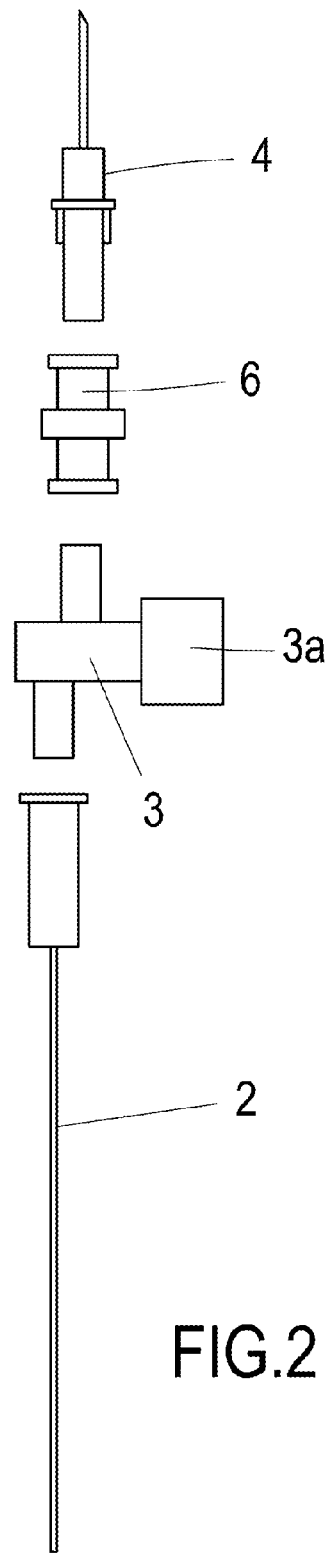

It is another object of the invention to provide an extraction device for extracting material from the first container to the second container. FIGS. 1 and 2 show a schematic view of an embodiment of said inventive extraction device, shown as an assembly and in breakdown form respectively. The extraction device mainly comprises a first needle (2) to be inserted in the first container in accordance with the method, a second needle (4) to be inserted in the second container in accordance with the method, and a means that may be operated by a user to open and close the passage of material from the first needle (2) to the second needle (4). Generally, the first needle (2) is provided with a bevelled tip in the event that the method is to be performed in a sealed environment, in other words with the first container sealed (thereby enabling said bevelled tip to perforate the cap of the first container). If, however, the method is to be performed in an open environment (by opening the first container once it has been centrifuged) it is not necessary for the first needle (2) to have a bevelled tip. Preferably, the means for opening and closing the passage of material from the first needle (2) to the second needle (4) is a switch-unit (3) provided with a button (3a), as shown in the figures, enabling easy and efficient use of the device.

In the embodiment shown the system comprises a connector (6) for adapting the male connection of the second needle (4) to the male connection of the switch-unit (3). This connector (6) is, of course, not always necessary.

Preferably, the device also comprises a casing (1) from which the first needle (2) projects. The casing (1) allows the means for opening and closing the passage of material from the first needle (2) to the second needle (4) to be operated. In the embodiment shown, for example, the button (3a) of the switch-unit (3) projects from the casing (1) and may be easily operated by the user of the device.

Figure 3:
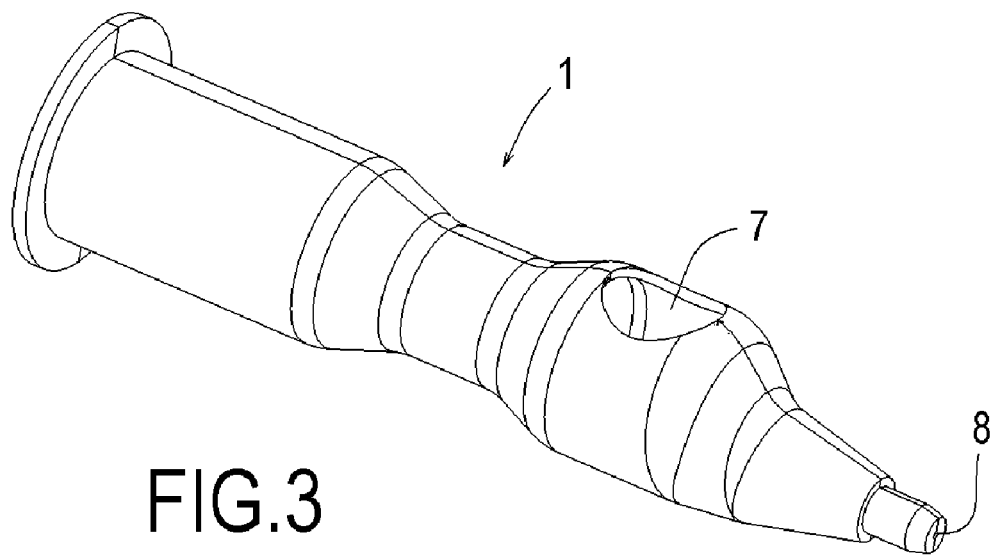
FIGS. 3 and 4 respectively show a complete and partial perspective of the casing comprised in the embodiment of FIG. 1.
Figure 4:
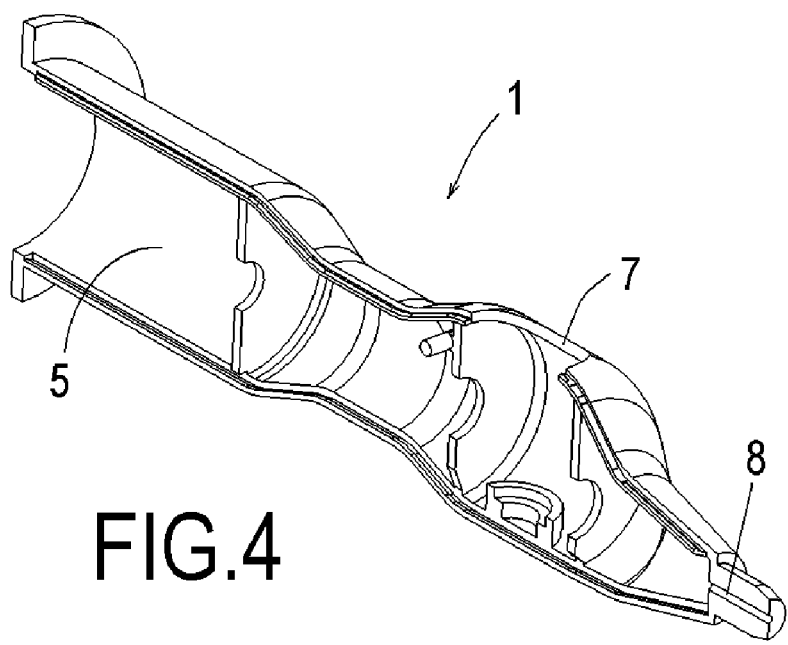

Preferably the casing (1) also comprises a housing area (5) meant to receive (totally or partially) the second container in accordance with the method. Said housing area (5) can also be seen in FIG. 4, which shows a partial perspective of the casing (1) shown in FIG. 1. FIG. 3 shows a perspective of the whole casing (1), where the hole (7) through which the button (3a) of the switch-unit (3) projects and the hole (8) through which the first needle (2) projects may be seen.

The casing (1) may also comprise holes to enable the insertion of an air-venting system and means for guiding the air-venting system to the first container. The air-venting system, which allows the intake of small amounts of filtered air, is useful when the inventive procedure is performed with the first container sealed, in cases where the passage of material must not be interrupted by the equalling of pressures between the first container and the second container.

The system shown is used as follows. The second container is inserted into the housing area (5) and, by exerting sufficient pressure on it, the second needle (4) is able to perforate the cap of said second container. The first needle (2) is then inserted in the first container (open or closed). The button (3a) of the switch unit (3) is then pressed, with the material (according to the inventive procedure) being transferred from the first container to the second container as a result of the difference in pressures.

The invention claimed is:

1. Method for the preparation of at least one compound from blood, characterised in that it comprises the following steps:

i) providing blood in a first sealed container with a pressure below atmospheric pressure;

ii) separating the blood into at least the following fractions: a fraction of red blood cells in the bottom part of the first container, a fraction of white blood cells and platelets above the preceding one and, above, a plasma fraction with a platelet gradient concentration, said gradient decreasing towards the top part of the first container;

iii) inserting an extraction device substantially up to the top level of the highest fraction contained in the first container;

iv) performing, at least once, the steps of connecting a second container that is vacuum-sealed and has a pressure below that of the first container to the extraction device; waiting for a certain period of time until a required amount of plasma, white blood cells and platelets and/or red blood cells is/are transferred, as a result of the difference in pressures, to the second container;

removing the second container; and, in the event of further extractions being performed, adjusting the degree to which the extraction device is introduced so that it once again reaches the top level of the remaining fractions.

2. Method for the preparation of at least one compound from blood, according to claim 1, wherein the first container is opened following the separation of blood into fractions and before the introduction of the extraction device.

3. Method for the preparation of at least one compound from blood, according to claim 1, characterised in that all the steps are performed in accordance with a closed system.

4. Method for the preparation of at least one compound from blood, according to claim 3, characterised in that along with the extraction device an air-venting system is introduced in the first container to allow the intake of filtered air in said container and ensure that the pressure of the first container is always higher than that of the second container.

5. Method for the preparation of at least one compound from blood, according to claim 3, characterised in that the extraction device comprises a Septum to keep the circuit sealed.

6. Method for the preparation of at least one compound from blood, according to claim 1, characterised in that the first container contains at least one anticoagulant.

7. Method for the preparation of at least one compound from blood, according to claim 1, characterised in that the first container does not contain an anticoagulant.

8. Method for the preparation of at least one compound from blood, according to claim 1, characterised in that the second container contains at least one coagulant, procoagulant, activating agent or any other biomaterial or agent, either prior to the transfer from the first container or added at a later stage.

9. Method for the preparation of at least one compound from blood, according to claim 1, characterised in that the second container contains at least one coagulation accelerator.

10. Method for the preparation of at least one compound from blood, according to claim 1, characterised in that the blood is separated into fractions by sedimentation.

11. Method for the preparation of at least one compound from blood, according to claim 1, characterised in that the blood is separated into fractions by centrifuging the first container.

12. Method for the preparation of at least one compound from blood, according to claim 11, characterised in that the first container is centrifuged at a centrifugation speed of between 100 and 900 G for a time of 3 to 12 minutes.

13. Method for the preparation of at least one compound from blood, according to claim 12, characterised in that the first container is centrifuged at a centrifugation speed of between 300 and 800 G for a time of 5 to 9 minutes.

* * * * *